United States Patent [19]

Davidson

[11] Patent Number: 4,889,951

[45] Date of Patent: Dec. 26, 1989

[54] PERFLUOROALKYLATION PROCESS

[75] Inventor: Robert I. Davidson, Baton Rouge, La.

[73] Assignee: Ethyl Corporation, Richmond, Va.

[21] Appl. No.: 185,399

[22] Filed: Apr. 25, 1988

Related U.S. Application Data

[62] Division of Ser. No. 808,204, Dec. 12, 1985, Pat. No. 4,822,904.

[51] Int. Cl.$^4$ ............................................. C07C 121/62
[52] U.S. Cl. ..................................... 562/427; 558/378
[58] Field of Search ......................... 558/378; 562/427

[56] References Cited

U.S. PATENT DOCUMENTS 3,408,411 10/1968 McLoughlin et al. .............. 260/646
4,439,617 3/1984 Sestanj et al. .......................... 560/39

OTHER PUBLICATIONS

McLoughlin, et al.; Tetrahedron, 25, (1969), pp. 5921-5940.
Gassman, et al.; Tetrahedron Letters, 26, (1985), pp. 5243-5246.
Kobayashi, et al.; Tetrahedron Letters, 42, (1979), pp. 4071-4072.
Matsui, et al.; Chemistry Letters, (1981), pp. 1719-1720.

*Primary Examiner*—Joseph Paul Brust
*Attorney, Agent, or Firm*—Patricia J. Hogan

[57] ABSTRACT

Perfluoroalkylaromatic compounds containing at least two carbons in the perfluoroalkyl group are prepared by reacting an aromatic bromide or iodide with a potassium perfluoroalkanoate corresponding to the formula $KOOC(CF_2)_nCF_3$ wherein n is an integer of at least one in the presence of cuprous iodide and a dipolar aprotic solvent.

5 Claims, No Drawings

PERFLUOROALKYLATION PROCESS

This is a division of Ser. No. 808,204, filed 12/12/85, now U.S. Pat. No. 4,822,904, issued 4/18/89.

FIELD OF INVENTION

This invention relates to perfluoroalkylaromatic compounds and more particularly to a process for preparing them.

BACKGROUND

As disclosed in McLoughlin et al., *Tetrahedron*, Vol. 25, pp. 5921–5940, 1969, Kobayashi et al., *Tetrahedron Letters*, No. 42, pp. 4071–4072, 1979, Gassman et al., *Tetrahedron Letters*, Vol. 26, No. 43, pp. 5243–5246, 1985, and U.S. Pat. Nos. 3,408,411 (McLoughlin et al.) and 4,439,617 (Sestanj et al.), it is known that perfluoroalkylaromatic compounds are apt to be useful as biologically-active compounds, surfactants, coatings, sealants, dyestuffs, alkyd-type resins, etc.; and they can be prepared in various ways. Matsui et al., *Chemistry Letters*, 1981, pp. 1719–1720, teach that aromatic halides may be trifluoromethylated with sodium trifluoroacetate in the presence of cuprous iodide and a dipolar aprotic solvent. Copending application Ser. No. 724,474 (Ramachandran et al.), filed April 18, 1985, now U.S. Pat. No. 4,599,010, issued 05-20-86, discloses the use of the technique of Matsui et al. in trifluoromethylating 6-alkoxy-5-halo-1-cyanonaphthalenes and hydrocarbyl 6-alkoxy-5-halo-1-naphthoates.

SUMMARY OF INVENTION

An object of this invention is to provide a novel process for preparing perfluoroalkylaromatic compounds containing at least two carbons in the perfluoroalkyl group.

This and other objects are attained by (A) reacting an aromatic bromide or iodide with at least about one equivalent of a potassium perfluoroalkanoate corresponding to the formula:

$$KOOC(CF_2)_nCF_3$$

wherein n is an integer of at least one in the presence of cuprous iodide and a dipolar aprotic solvent and (B) if desired, subjecting the product to one or more additional reactions to form a derivative.

DETAILED DESCRIPTION

Aromatic halides utilizable in the practice of the invention are substituted and unsubstituted aromatic iodides and bromides wherein any substituents are inert substituents (i.e., substituents that do not prevent the reaction from occurring) such as alkyl, alkoxy, alkylthio, aryl, aryloxy, arylthio, cyano, nitro, acylamino, alkylamino, tertiary amino, sulfonamido, sulfone, sulfonyl, phosphino, perfluoroalkyl, chloro, fluoro, ester, aldehyde, ketone, acetal, sulfono groups, etc., and the aromatic ring may be a carbocyclic ring such as a benzene, naphthalene, anthracene, etc., ring or a five- or six-membered heterocyclic ring having aromatic character, e.g., a pyridine, quinoline, isoquinoline, thiophene, pyrrole, furan, etc., ring. Exemplary of such compounds are iodobenzene, 3-iodotoluene, 4-chloroiodobenzene, 4-iodomethoxybenzene, 1-iodonaphthalene, 3-iodoaniline, 1-iodo-3-nitrobenzene, 2-iodothiophene, 4-iodoisoquinoline, 2-iodopyridine, 3-iodoquinoline, the corresponding bromides, etc.

In a preferred embodiment of the invention, the aromatic halide is a halonaphthalene corresponding to the formula:

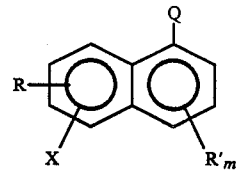

wherein R and R' are independently selected from chloro, fluoro, nitro, hydroxy, and alkyl and alkoxy substituents containing 1–6 carbons; Q is —CN or —COOR"; R" is saturated hydrocarbyl; X is bromo or iodo; and m is 0 or 1.

The halocyanonaphthalenes and halonaphthoates utilizable in the practice of the invention may be any compounds corresponding to the above halonaphthalene formula, but they are preferably compounds wherein m is 0, X is in the 5-position, and R is an alkyl or alkoxy substituent in the 6-position. When the R and R' substituents are alkyl or alkoxy, they are generally straight-chain groups of 1–3 carbons or branched-chain groups of three or four carbons, such as methyl, ethyl, propyl, 1-methylethyl, butyl, 2-methylpropyl, 1,1-dimethylethyl, the corresponding alkoxy groups, etc., although, as indicated above, larger groups such as hexyl and hexanoxy are also utilizable. When the halonaphthalene is an ester, R" may be any saturated hydrocarbyl group (i.e., a hydrocarbyl group that is free of aliphatic unsaturation) but is preferably an alkyl, cycloalkyl, aryl, alkaryl, or aralkyl group containing 1–10 carbons, e.g., methyl, ethyl, propyl, cyclohexyl, phenyl, tolyl, benzyl, etc. Particularly preferred halonaphthalenes are 6-alkoxy-5-bromo-1-cyanonaphthalenes, 6-alkoxy-5-iodo-1-cyanonaphthalenes, 6-alkoxy-5-bromo-1-naphthoates, and 6-alkoxy-5-iodo-1-naphthoates, especially those compounds wherein the alkoxy groups are methoxy.

The halonaphthoates are known compounds. The halocyanonaphthalenes are compounds that can be prepared by cyanating the appropriately substituted tetralone, e.g., 6-methoxytetralone, to form the appropriately substituted 1-cyano-3,4-dihydronaphthalene, e.g., 6-methoxy-1-cyano-3,4-dihydronaphthalene, aromatizing the product in any suitable manner, and brominating or iodinating the resultant substituted 1-cyanonaphthalene by known techniques.

As already mentioned, the halonaphthalene or other aromatic halide is reacted with at least about one equivalent of a potassium perfluoroalkanoate to form the corresponding perfluoroalkylaromatic compound. Since there does not appear to be any maximum to the number of $CF_2$ groups that can desirably be incorporated into the aromatic molecule, the potassium perfluoroalkanoate employed in the reaction may be any compound corresponding to the formula $KOOC(CF_2)_nCF_3$ wherein n is an integer of at least one, and it is generally the salt which contains the same number of $CF_2$ groups as is desired in the product. However, because of cost and availability factors, as well as the fact that the reaction typically permits the formation of at least some perfluoroalkylaromatic compound containing more $CF_2$ groups in the substituent than are present in the perfluoroalkanoate, the preferred reactants are those containing about 1-16 CF$_2$ groups, such as potassium pentafluoropropionate, heptafluorobutyrate, nonafluorovalerate, tridecafluoroheptanoate, pentadecafluorooctanoate, heptadecafluorononanoate, nondecafluorodecanoate, etc. There does not appear to be any maximum to the amount of salt that may be employed. However, as a practical matter, the amount used is generally in the range of about 1-20 equivalents, preferably at least about 1.5 equivalents.

Dipolar aprotic solvents that may be utilized include, e.g., N-methylpyrrolidone, N,N-dimethylformamide, N,N-dimethylacetamide, hexamethylphosphoric triamide, dimethylsulfoxide, etc., but the particular solvent employed does not appear to be critical except in the sense that it should have an appropriate boiling point for use at the reaction temperatures to be utilized. The solvent is used in solvent amounts, e.g., an amount such as to provide an organic solids concentration of up to about 15%.

The cuprous iodide may be employed in any suitable amount, generally an amount in the range of about 0.5-5 equivalents.

The reaction is conducted by combining the ingredients in any convenient order and heating them at a suitable temperature, conveniently reflux temperature, to accomplish the desired perfluoroalkylation. Anhydrous conditions are preferably employed, and the temperature is generally in the range of about 130°-160° C., preferably about 40°-155° C.

The perfluoroalkylnaphthalene products of the preferred reaction, like their trifluoromethyl homologs, can be subjected to reactions such as those taught by Sestanj et al., the teachings of which are incorporated herein in toto by reference. Thus, e.g., (1) a (perfluoroalkyl)cyanonaphthalene or perfluoroalkyl-naphthoate prepared by the perfluoroalkylation reaction may be hydrolyzed to the corresponding acid in the presence of a base such as sodium or potassium hydroxide, (2) the acid can be halogenated, e.g., by reaction with thionyl chloride, to form the corresponding acid halide, (2) the acid halide may be reacted with a saturated hydrocarbyl ester of an acid corresponding to the formula ZNHCH$_2$COOH (e.g., methyl, ethyl, propyl, cyclohexyl, phenyl, tolyl, or benzyl sarcosinate, the corresponding esters of aminoacetic acids having other N-substituents containing 1-6 carbons, such as N-ethyl, N-propyl, etc.) to form an amide corresponding to the formula:

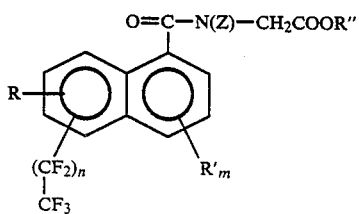

(3) the amide may be saponified to form the corresponding salt, then hydrolyzed to the corresponding acid, and then thiated, e.g., with phosphorus pentasulfide or the like, to form a thioamide corresponding to the formula:

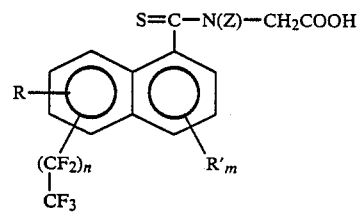

or (4) the thioamide may be prepared by thiating the amide and then subjecting the product to the saponification and hydrolysis steps.

The invention is advantageous in that it provides a means of preparing perfluoroalkyl compounds useful in various applications, such as surfactants, coatings, sealants, resins, dyestuffs, etc., as well as biologically-active materials or precursors therefor.

The following examples are given to illustrate the invention and are not intended as a limitation thereof.

EXAMPLE I

A suitable reaction vessel was charged with 8.1 g of 6-methoxy-5-bromo-1-cyanonaphthalene, 11.8 g of CuI, 35 ml of toluene, and 55 ml of N,N-dimethylformamide. The reaction mixture was heated to 165° C. with concurrent azeotropic removal of toluene/water (25 ml) and then maintained at 155° C. when 11.8 g of potassium pentafluoropropionate was added. The reaction was monitored by VPC. After five hours no starting material was detected and the reaction mixture was poured into 150 ml of water and 125 ml of methylene chloride. The two phases were filtered, after which the organic layer was separated, washed with brine, and concentrated in vacuo to provide a crude 6-methoxy-5-pentafluoroethyl-1-cyanonaphthalene (6-MPCN) having a purity of greater than 95%.

EXAMPLE II

The crude 6-MPCN product of Example I was dissolved in 135 ml of methanol and 40 ml of a potassium hydroxide solution (4.5 g of KOH in 40 ml of water) and heated to 125° C./70 psi for seven hours. The reaction mixture was then worked up and acidified to yield 6.6 g of 6-methoxy-5-pentafluoroethyl-1-naphthoic acid.

It is obvious that many variations may be made in the products and processes set forth above without departing from the spirit and scope of this invention.

What is claimed is:

1. In a process for preparing a thioamide-acid corresponding to the formula:

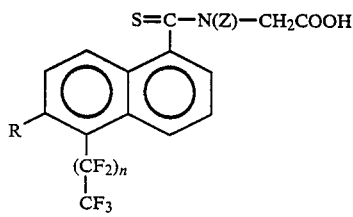

by (A) reacting a halocyanonaphthalene corresponding to the formula:

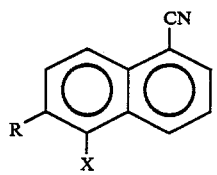

with a perfluoroalkanoate to replace the X with a perfluoroalkyl group, (B) hydrolyzing the perfluoroalkylated nitrile to the corresponding acid, (C) halogenating the acid to the corresponding acid halide, (D) reacting the acid halide with a saturated hydrocarbyl ester of an acid corresponding to the formula $ZNHCH_2COOH$ to form an amide-ester, (E) thiating the amide-ester, and (F) subjecting the product to saponification and hydrolysis to form the thioamide-acid, the improvement which comprises conducting the perfluoroalkylation by reacting the halocyanonaphthalene with at least about one equivalent of a potassium perfluoroalkanoate corresponding to the formula $KOOC(CF_2)_nCF_3$, wherein n is an integer of 1–16, at about 130°–160° C. in the presence of about 0.5–5 equivalents of cuprous iodide in a dipolar aprotic solvent so as to form a perfluoro-alkylnaphthalene corresponding to the formula:

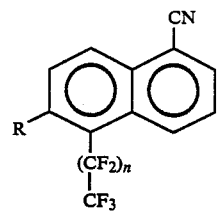

in which substituted naphthalene formulas R is an alkoxy substituent containing 1–6 carbons, X is bromo or iodo, Z is an alkyl group containing 1–6 carbons, and n is an integer of 1–16.

2. The process of claim 1 wherein the halocyanonaphthalene is a 6-alkoxy-5-bromo-1-cyanonaphthalene.

3. The process of claim 2 wherein the alkoxy group is methoxy.

4. The process of claim 1 wherein the halocyanonaphthalene is a 6-alkoxy-5-iodo-1-cyanonaphthalene.

5. The process of claim 4 wherein the alkoxy group is methoxy.

* * * * *